United States Patent
Gravenstein et al.

(10) Patent No.: US 8,818,472 B2
(45) Date of Patent: Aug. 26, 2014

(54) METHODS AND DEVICES FOR NONINVASIVE MEASUREMENT OF ENERGY ABSORBERS IN BLOOD

(75) Inventors: Dietrich Gravenstein, Gainesville, FL (US); Mark Rice, Jacksonville, FL (US); Samsun Lampotang, Gainesville, FL (US); Nikolaus Gravenstein, Gainesville, FL (US); Lori Deitte, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 801 days.

(21) Appl. No.: 12/679,721

(22) PCT Filed: Sep. 29, 2008

(86) PCT No.: PCT/US2008/011276
§ 371 (c)(1),
(2), (4) Date: May 11, 2010

(87) PCT Pub. No.: WO2009/045374
PCT Pub. Date: Apr. 9, 2009

(65) Prior Publication Data
US 2010/0286515 A1    Nov. 11, 2010

Related U.S. Application Data

(60) Provisional application No. 60/976,038, filed on Sep. 28, 2007.

(51) Int. Cl.
*A61B 5/00*      (2006.01)
(52) U.S. Cl.
USPC .......................................... 600/310; 600/322
(58) Field of Classification Search
USPC ............ 600/310, 322–4, 326, 328, 330, 331, 600/322–34; 356/41
See application file for complete search history.

(56) References Cited

U.S. PATENT DOCUMENTS 5,833,602 A * 11/1998 Osemwota .................... 600/310
6,240,306 B1    5/2001 Rohrscheib et al.
(Continued)

OTHER PUBLICATIONS

Written Opinion of corresponding Application Serial No. PCT/US2008/011276 mailed Apr. 8, 2010.
(Continued)

*Primary Examiner* — Elmer Chao
(74) *Attorney, Agent, or Firm* — Alston & Bird LLP

(57) ABSTRACT

Various embodiments of the present invention include devices for use in determining the concentration of a tissue energy absorber (e.g., hemoglobin) in an individual's blood. In particular embodiments, the device includes a photometric device (e.g., a pulse oximeter) and an imaging device (e.g., an ultrasound imaging device or other suitable imaging device), and the device is adapted for: (A) using the photometric device to measure a change in mass of the tissue energy absorber within a particular volume of the individual's blood between a first point in time and a second point in time, the particular volume of blood being blood within a particular portion of at least one vascular structure, the vascular structure comprising at least one of the individual's vessels (e.g., at least one of the individual's arteries); (B) using an ultrasound imaging device to measure a change in interior volume, between the first point in time and the second point in time, of the particular portion of the vascular structure; and (C) using both the measured change in the mass of the tissue energy absorber, and the measured change in interior volume to determine at least an approximate blood total concentration of the tissue energy absorber within the individual's blood.

35 Claims, 10 Drawing Sheets

(56) References Cited

U.S. PATENT DOCUMENTS

| | | |
|---|---|---|
| 6,289,230 B1 | 9/2001 | Chaiken et al. |
| 6,751,490 B2 | 6/2004 | Esenaliev et al. |
| 2007/0093702 A1 | 4/2007 | Yu et al. |

OTHER PUBLICATIONS

International Search Report and Written Opinion of corresponding Application Serial No. PCT/US2008/011276 mailed May 26, 2009.

* cited by examiner

Diastole

Systole

METHODS AND DEVICES FOR NONINVASIVE MEASUREMENT OF ENERGY ABSORBERS IN BLOOD

FIELD OF THE INVENTION

Various embodiments of the present invention pertain to the field of noninvasive in vivo measurement of energy absorbers in blood.

BACKGROUND OF THE INVENTION

Human tissues can absorb many forms of energy including heat, sound, and light. Blood is one tissue that contains many absorbers of light energy. The hemoglobin molecules in the blood have extensively characterized spectrophotometric signatures and can be identified by the strength and wavelength of their absorptions. Contemporary clinical laboratory medicine relies on these physical properties of light energy absorption for the routine measurement of bilirubin, oxyhemoglobin (HbO2), deoxyhemoglobin (Hb), methemoglobin (metHb), carboxyhemoglobin (COHb), fetal hemoglobin (FHb), total hemoglobin (THb), and oxygen saturation (SaO2 [%]) in blood.

Hemoglobin, found in all animal blood, is the molecule responsible for collecting oxygen in the lungs and carrying it to the tissues. There, it releases the oxygen and picks up carbon dioxide. After returning to the lungs, the carbon dioxide is released and oxygen picked up once again. Hemoglobin production and loss can be affected by many conditions and explains why it is among the most commonly measured parameters in clinical medicine.

Blood total hemoglobin concentration ([THb]) is reported as grams of hemoglobin per deciliter of blood (g/dL). Patients frequently present either with previously unknown abnormalities in [THb], such as from iron deficiency anemia, or the [THb] becomes abnormal during their clinical course. For example, in the operating room, the change in [THb] can be rapid, difficult to identify, and hard to measure in a timely fashion. Examples of these situations include acute trauma with massive blood loss, large orthopedic surgical cases, and liver transplantation. In each of these examples, as well as many others, blood loss may be rapid, so that identifying the change in [THb] and correcting the abnormal [THb] quickly may be critical to patient survival.

Measurement of the various hemoglobin species concentrations in blood ([HbO2], [Hb], [metHb], [COHb]) allows an accurate assessment of blood oxygen content ([HbO2]×Vol) and oxygen saturation (SaO2=[HbO2]/([HbO2]+[Hb]+[metHb]+[COHb])×100%, or SpO2=[HbO2]/([HbO2]+[Hb])×100%. Carboxyhemoglobin concentration ([COHb]) can be dangerously elevated in tobacco smokers, house fire victims, firefighters, and attempted suicide victims. This condition does not reduce [THb] but effectively reduces the [HbO2] available for oxygen delivery to the tissues and can require aggressive intervention.

The current method of [THb] measurement is invasive and requires the drawing of a blood sample from the artery, vein, or fingertip of a patient, analysis of that sample by means of a laboratory test, and delivery of the subsequent result to the healthcare provider. This process is painful to awake patients and risks needle stick exposures to care providers. Furthermore, it is costly, time-consuming and distracting to the clinical care provider and can result in delayed patient care. Lastly, in a dynamic clinical situation, the patient's [THb] may continue changing between blood sampling and reporting so that critical decisions may be based on outdated information.

An accurate, clinically continuous noninvasive measurement of [THb], at a reasonable cost, would be a major step forward in healthcare technology. There would be widespread application for this device in the operating room and in a number of other clinical settings ranging from outpatient clinics to third-world countries where anemia screening is a major problem. It would thus be desirable to obtain fast and reliable measurements of the blood hemoglobin concentration through simple, noninvasive testing.

SUMMARY OF THE INVENTION

Various embodiments of the present invention provide a solution to one or more of the above deficiencies in current technologies. For example, a more accurate measurement of blood total hemoglobin concentration [THb] can be made by measuring pulse-added blood volume ($\Delta V$) with each cardiac cycle by directly imaging an artery and/or vein and calculating the change in blood volume with each heartbeat. Or, the volume of vein(s) within the light path of a photometric system can be used as the primary signal. In either implementation, instead of a measurement through an entire heterogeneous and optically complex tissue or limb, various embodiments of the present invention measure scattered and reflected light from one or more specific imaged vessels. In one embodiment, the present invention augments the arterial pulsation and substantially eliminates venous blood contributions by placing pressure directly on the portion of the artery measured. Furthermore, various embodiments of the invention incorporate both an ultrasound device (e.g., for measuring the volume of a portion of a vessel) and a photometric device (e.g., for measuring the mass of a particular energy absorbing tissue, such as hemoglobin) into a single device. In various embodiments, this may help reduce construction costs and result in an "easy to use" device.

Particular embodiments of the present invention associate the measurement of blood volumes ($\Delta V$) utilizing ultrasound imaging with an associated measurement of light energy, in the form of light that is transmitted, scattered (forward-scattered or back-scattered), and/or reflected as it proceeds from a light source (e.g., a laser or other suitable light source) to a sensor (e.g., a photodetector). Exploiting the absorption of light, predominantly in the red through infrared (IR) spectrum, by hemoglobin, particular embodiments of this invention measure the concentration of energy absorbers (e.g., the blood total hemoglobin concentration) in a rapidly-repeatable, noninvasive manner. Furthermore, particular embodiments of the present invention measure the mass and volume measurements only through one or more particular identified vascular compartments. For superficial vascular structures, in particular embodiments, a direct measurement of intravascular (arterial and/or venous) change in volume is possible, which eliminates confounding noise from other energy scattering or absorbing elements such as subcutaneous tissues, membranes, and adipose.

In particular embodiments, the photometric device (e.g., pulse oximeter or other suitable photometric device) and ultrasound measurement devices are combined into one unit, so that volume measurements made by the photometric device are made at the same site and time as corresponding mass measurements. In a particular embodiment, the ultrasound device may be used to measure the volume of a particular portion of a vessel at a first particular point in time, while the photometric device measures (e.g., at this "first point in time", or a second point in time that is within about one second of the second point in time) the mass of a particular energy absorbing tissue (e.g., hemoglobin) within a portion of the vessel that at least generally corresponds to the particular portion of the vessel measured by the ultrasound device. In particular embodiments, this process is repeated at least twice per cycle of the device.

In particular embodiments: (1) in the first iteration of the process during a particular cycle, the ultrasound device is used to measure the volume of a particular portion of a vessel at a time during which the particular portion of the vessel is in a substantially diastolic (e.g., diastolic) orientation; and (2) in the second iteration of the process during a particular cycle, the ultrasound device is used to measure the volume of a particular portion of the vessel at a time during which the particular portion of the vessel is in a substantially systolic (e.g., systolic) orientation.

Also, in particular embodiments: (1) in the first iteration of the process during a particular cycle, the photometric device is used to measure the mass of an energy absorbing tissue (e.g., hemoglobin) within a volume of blood that at least generally corresponds to (e.g., corresponds to) the volume of blood within the particular portion of the vessel at a time during which the particular portion of a vessel is in a substantially diastolic (e.g., diastolic) orientation; and (2) in the second iteration of the process during a particular cycle, the photometric device is used to measure the mass of an energy absorbing tissue (e.g., hemoglobin) within a volume of blood that at least generally corresponds (e.g., corresponds to) the volume of blood within the particular portion of the vessel at a time during which the particular portion of the vessel is in a substantially systolic (e.g., systolic) orientation.

The information taken from the ultrasound device during this cycle may be used to determine the change in the volume of blood within the portion of the vessel between a time, within a particular cardiac cycle, that the vessel is in a substantially diastolic (e.g., diastolic) orientation and a time, within the particular cardiac cycle, that the vessel is in a substantially systolic (e.g., systolic) orientation. Also, the information from the photometric device may be used to determine (or at least approximate) the change in mass of an energy absorbing tissue within the portion of the vessel between the time that the vessel is in a substantially diastolic (e.g., diastolic) orientation (e.g., within the particular cardiac cycle referenced above) and the time that the vessel is in a substantially systolic (e.g., systolic) orientation (e.g., within the particular cardiac cycle referenced above). In particular embodiments, the photometric device is a pulse oximeter, and the change in mass of the energy absorbing tissue during pulsatile flow is determined (or estimated) based, at least in part, on the area under a plethysmogram curve (AUC) generated by the pulse oximeter, normalized to the DC signal.

This "change in volume" and "change in mass" information may then be used to determine (or at least approximate) the patient's blood total concentration for the energy absorbing tissue (e.g., hemoglobin). This may be done, for example, by dividing the calculated change in mass by the calculated change in volume. In various embodiments, this process may be repeated over a plurality of a particular individual's cardiac cycles to provide an ongoing (e.g., at least substantially continuous), non-invasive indication of the patient's blood total hemoglobin concentration.

Alternatively, a database may be developed that includes the relationship, for particular patients at different points in time, between: (1) the ratio of the change in mass of a particular energy absorbing tissue to change in volume as measured as discussed above, and (2) the actual blood total concentration for the particular energy absorbing tissue as measured by conventional methods (e.g., through a conventional analysis of a blood sample from the particular patient). This database may then be used (e.g., using any suitable mathematical techniques) to convert future measured $\Delta m/\Delta v$ ratios derived from the methods described herein (or similar methods) to an approximate value of blood total concentration for the particular energy absorbing tissue.

It should be understood that, although at least one exemplary process described above involves measuring change in volume and change in mass between the time that a vessel is in a diastolic orientation and the time that the vessel is in a systolic orientation, the device may be used to calculate change in volume and change in mass between times in which the vessel is in any other two suitable orientations.

In another embodiment of the present invention, it is possible to take advantage of the augmentation of the volume and mass signal variation by exerting direct pressure over the segment of the artery being measured. In yet another embodiment of the invention, pressure is exerted directly over the artery and with pressure, venous structures that had contributed to the light signal variation are partially or fully collapsed, yielding a robust arterial signal (AC-type or DC-type of measurement) with reduced or no venous component signal that may augment or replace the measurement of the noncompressed vessels. In a further embodiment, arterial and venous signals can be measured separately. Utilizing the ultrasound to measure arterial flow, coupled with arterial [HbO2], and venous [HbO2], tissue oxygen extraction can be measured. This may have great utility in the critical care setting to direct therapy. With the measurement of arterial flow, coupled to arterial vessel diameter and pressure, obtained either from a second site or from the pressure transducer embedded in particular embodiments of the disclosed invention, peripheral vascular resistance can be calculated.

Thus, particular embodiments of the present invention combine the mass measurement of energy absorbers, such as hemoglobin, by photometric means with the direct measurement of the change in blood volume with high frequency (e.g., greater than about 8 MHz) ultrasound imaging of an artery and/or veins to make an accurate measurement of energy absorber concentration. In the specification, the radial artery is used as an example of an artery to be used with particular embodiments of the present invention. However, any suitable vessel (e.g., any vessel that may be imaged with an ultrasound transducer) may be used with various embodiments of the present invention.

Further objects, features, and advantages of particular embodiments of the invention will be apparent from the following detailed description when taken in conjunction with the accompanying drawings.

BRIEF DESCRIPTION OF THE DRAWINGS

Figure 1:
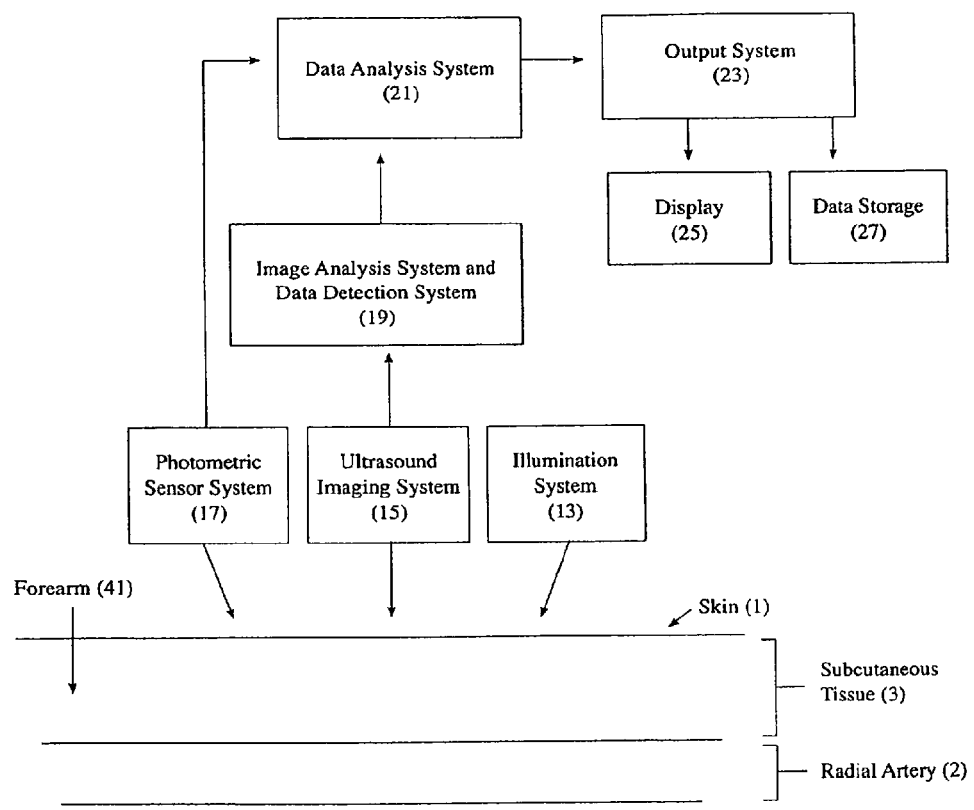

Having thus described the invention in general terms, reference will now be made to the accompanying drawings, which are not necessarily drawn to scale, and wherein:

FIG. 1 is a schematic diagram of an apparatus for measurement of blood energy absorbers in accordance with a particular embodiment of the invention.

Figure 2:
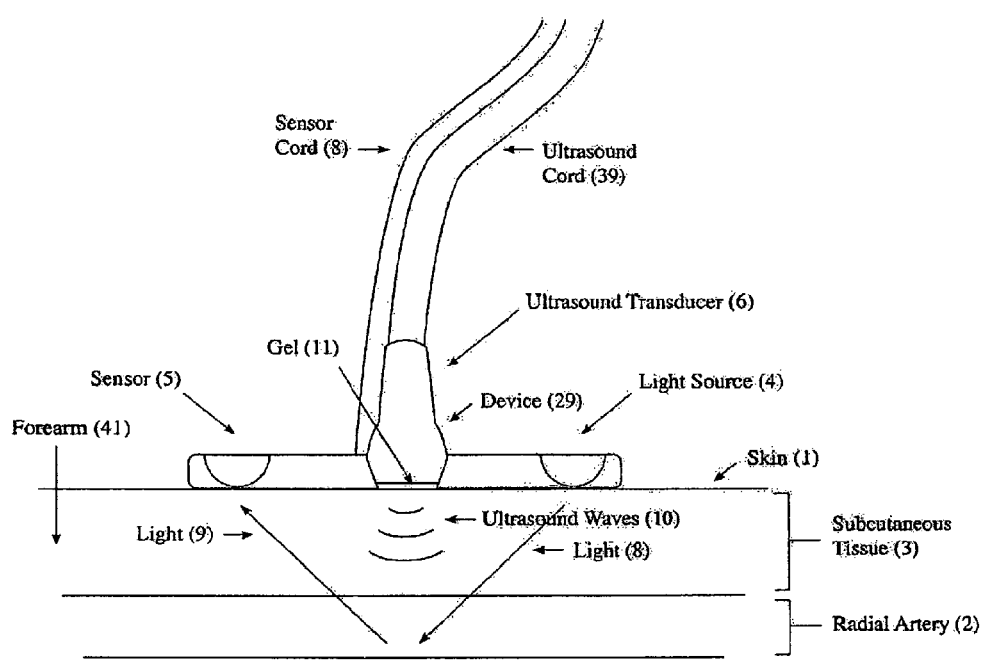

FIG. 2 is a schematic cross-sectional side view of a particular embodiment of the present invention including an axial cross-section of a patient's forearm, using the radial artery as an example for making the measurement.

Figure 3:
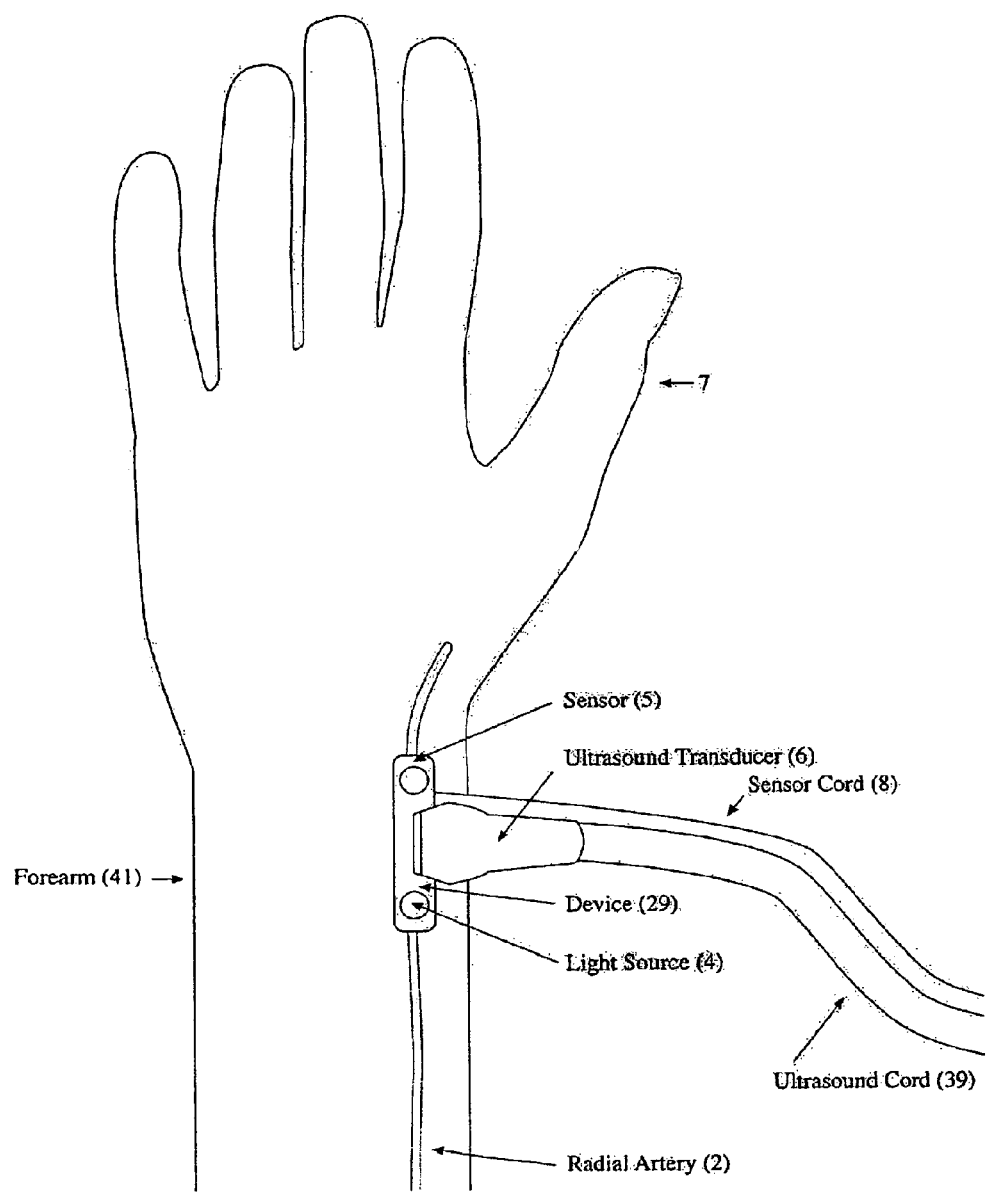

FIG. 3 is an illustrative top view of a device according to a particular embodiment of the invention.

Figure 4A:
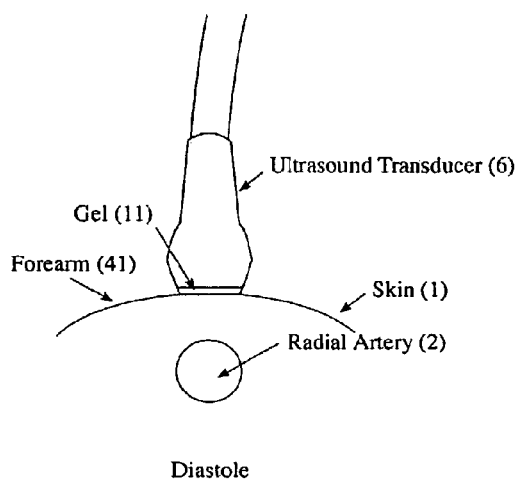
Figure 4B:
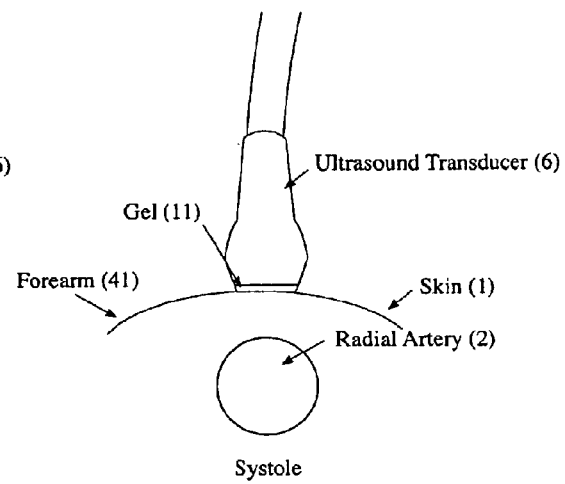

FIGS. 4A and 4B are cross-sectional views of a patient's forearm showing a schematic change in the radial artery diameter from diastole to systole (veins not shown).

Figure 5:
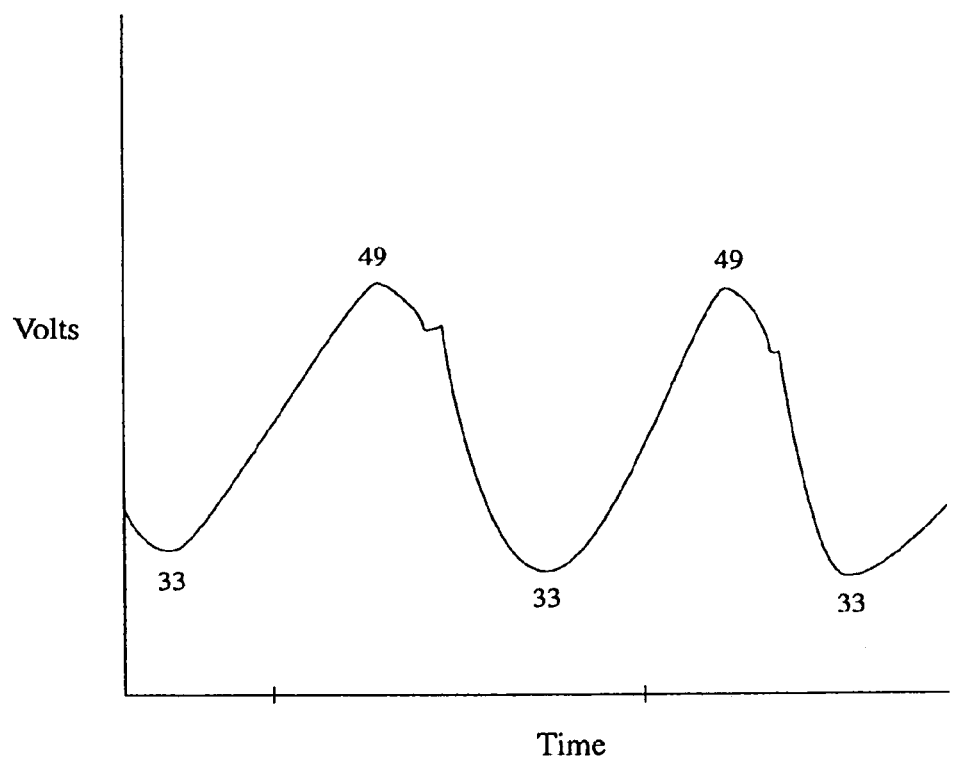

FIG. 5 indicates a photometric measurement as sensed by a light detector during a series of pulsatile artery measurements.

Figure 6:
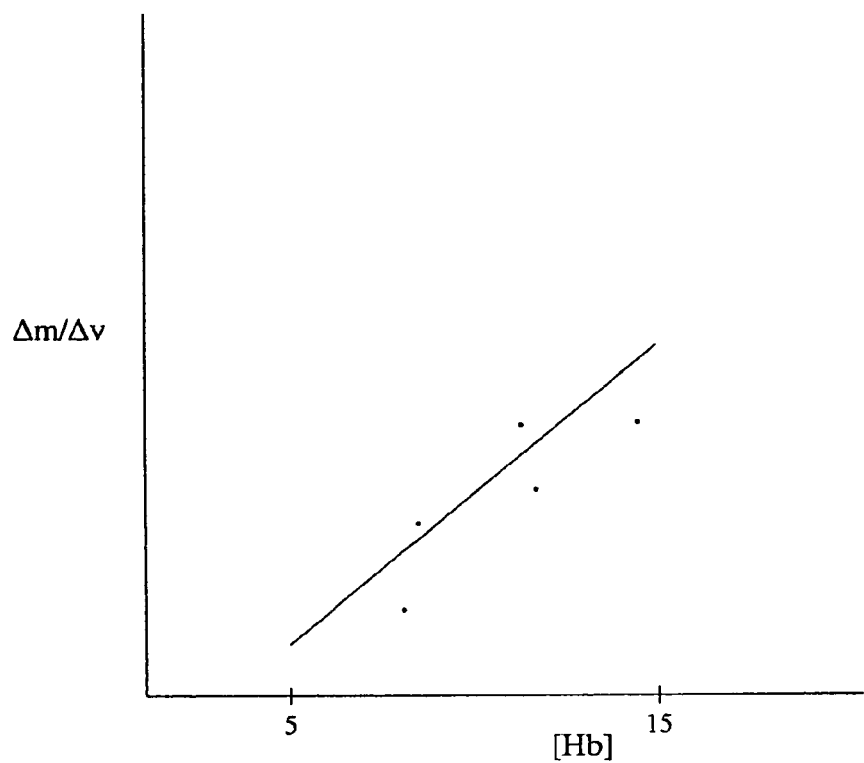

FIG. 6 is a sample graph of the ratio of Δm to Δv vs. blood total hemoglobin concentration.

Figure 7A:
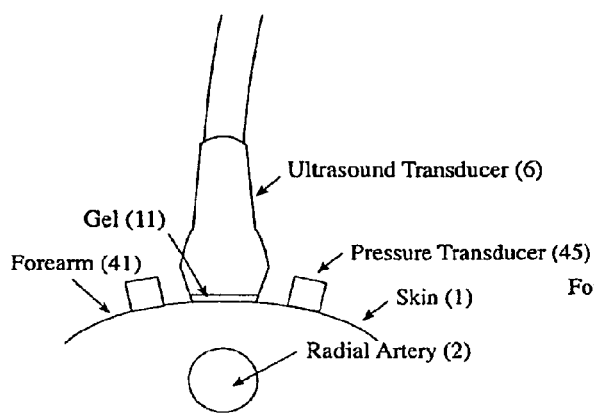
Figure 7B:
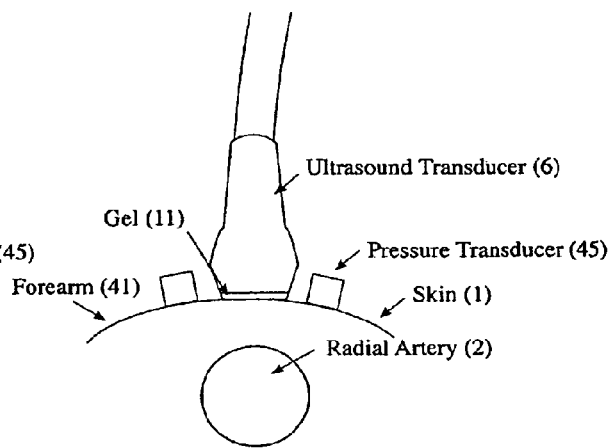

FIGS. 7A and 7B are cross-sectional views illustrating the effect of applying direct pressure while using various embodiments of the device. In particular, these figures show the augmentation of arterial pulsation during the same time periods of the cardiac cycle (veins not shown).

Figure 8:
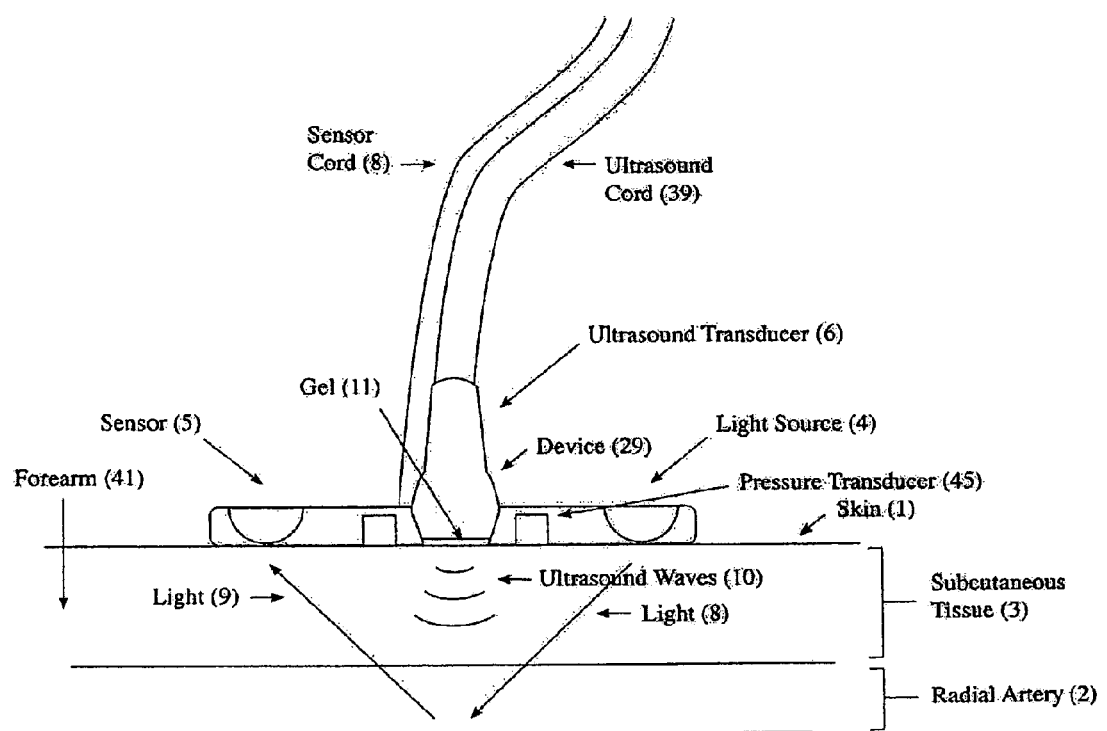

FIG. 8 is a cross sectional view showing an alternative embodiment of the device that comprises a pressure transducer, which is configured to be disposed directly over an artery targeted by the device. This pressure transducer measures the pressure applied adjacent the artery while the device is in use.

Figure 9A:
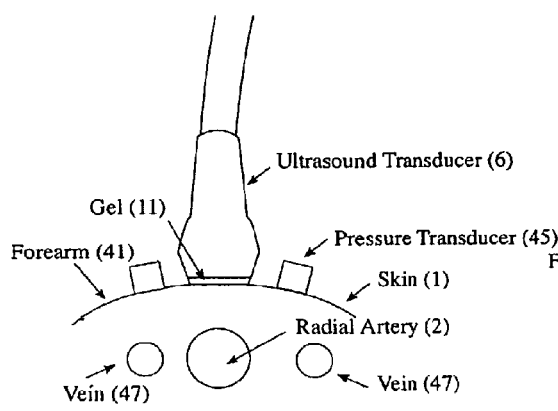
Figure 9B:
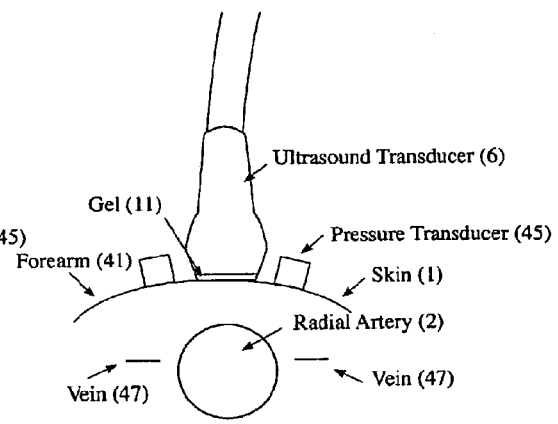

FIGS. 9A and 9B are cross-sectional views of another alternative embodiment of various embodiments of the invention showing pressure upon a target artery which results in the collapse of veins adjacent the artery.

Figure 10:
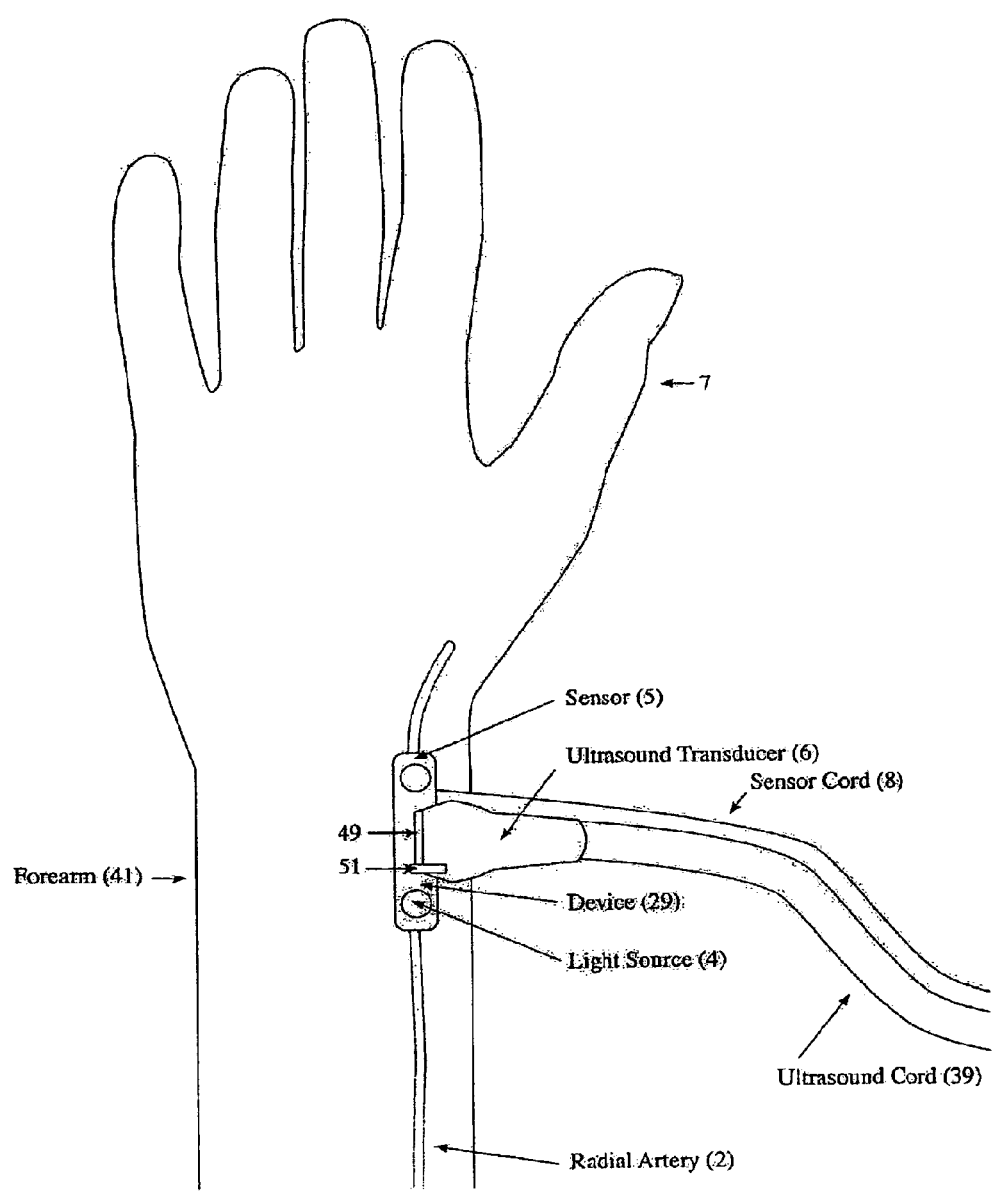

FIG. 10 is a top view of another alternative embodiment of the invention showing simultaneous imaging of both cross-sectional and longitudinal sections of the artery (veins not shown).

DETAILED DESCRIPTION OF VARIOUS EMBODIMENTS OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Ultrasound imaging has long been used for making cross-sectional measurements of body structures. However, only recently has ultrasound technology provided the accuracy to measure small superficial structures such as the radial artery. Recently developed ultrasound transducers, with high frequency rates (e.g., greater than 8 MHz and up to at least 55 MHz), are now available to very accurately image and allow measurement of small structures such as the cross-section of the radial artery and superficial veins. In fact, the resolution of one such transducer, the 55 MHz VisualSonics (Toronto, Canada) ultrasound transducer, is approximately 0.04 mm (40 micrometers). In addition, it has been shown that the radial artery changes in cross-section by approximately 5 to 10% from systole to diastole. Since the average internal diameter of a radial artery is approximately 1.5 millimeters, resolution of 0.04 mm by the measurement device yields very accurate measurements of the change in radial artery cross-section during the cardiac cycle. Veins, in contrast, with very low intravascular pressure, can be fully collapsed with little pressure, producing large vascular volume changes. By measurement of the cross-section, an accurate calculation can be made of the vascular volume change along the segment of the vessel or vessels that are measured by the light sensor.

In a particular early experiment by the inventors, the inventors discovered that a pulse oximeter probe (with the built-in light sources and light sensor) that is typically used to measure oxygen saturation through the width of a finger or through an earlobe, can be used to measure the blood oxygenation longitudinally along a patient's radial artery. The light sources and sensor were approximately 2 cm apart in one experiment, both facing the radial artery. With the sensor or the light sources (LEDs) facing the radial artery along the skin, a very robust signal was obtained from this geometry (sensitive tracing of an optoplethysmogram with the ability to detect each pulse and pulse oximeter readout). In fact, the signal was of similar quality to the tracing seen using the standard placement (transillumination configuration through an extremity) on the end of a patient's finger.

Devices, according to particular embodiments of the invention, are adapted to provide the measurement of both the change in mass of hemoglobin within a particular portion of a vessel, as measured via the change in light absorption with a light source (e.g., either an LED or a laser diode—and a photometric sensor) and the corresponding volume change ΔV of blood within the particular portion of the vessel (which may, for example, be calculated by measuring the portion of the vessel with an ultrasound transducer, such as a high-frequency ultrasound transducer). This measurement is preferably sufficiently accurate to accurately measure (or otherwise derive or approximate) blood total hemoglobin concentration.

In various embodiments, this measurement of blood total hemoglobin is made by specifically measuring the signal-producing vessels. These are typically superficial on an extremity where an artery or vein can be found to make the measurement (e.g., along the radial artery at the patient's wrist, or at arteries higher in the patient's arm, in the patient's neck, or in the patient's groin). The change in the volume of the vessel(s) (e.g., an artery and/or veins) can be ascertained by measurement of the long- and/or short-axis cross-section of the vessel in both distended (e.g., systole for arteries, uncompressed for veins) and collapsed (e.g., diastole for arteries, compressed for veins), along with the length of the vessel being measured. This can be approximated by the distance between the light source and the light sensor and the vessels' depth from the surface. Multiplying the length of the artery times the change in cross-section between distended and collapsed yields the change in intravascular volume (which corresponds to the volume of blood within the vessel). In various embodiments, the use of a plurality of ultrasound and optical sensors can be advantageously used to derive an even more accurate measurement of the volume (ΔV) and mass (ΔM) changes (for example, see FIG. 10).

With reference to the drawings, FIG. 1 illustrates one implementation of the apparatus of particular embodiments of the invention in conjunction with the forearm 41 of the patient, with the patient's skin 1 also shown in this example. It should be understood that although the radial artery in the forearm is used in the description of particular embodiments of the invention, any appropriate vessel (e.g., a vessel accessible by the photometric measurement and ultrasound imaging) may be used to practice various embodiments of the invention.

In this embodiment, the apparatus includes an energy delivery system (in this illustration, an illumination system 13) that is adapted for directing light with a wavelength that is absorbed by hemoglobin. In particular embodiments, to measure the mass of hemoglobin within a patient's bloodstream, the light is approximately 805 nm in wavelength, which is the isobestic point for hemoglobin, where both oxyhemoglobin and deoxyhemoglobin absorb light equally. By using this wavelength, the oxygenation level of the hemoglobin may have minimal to no influence on the blood hemoglobin measurement. Alternatively, the light source may comprise more than one wavelength of light at different wavelengths. The light source(s) may be a filament, fluorescent light, LED, laser diode or a laser. The illumination system 13 directs the light toward the vessel 2 to be measured at an angle that maximizes the signal detected by the photometric sensor system 17. This angle may vary depending on the particular vessel or vessel depth chosen for measurement.

The energy sensor, a photometric sensor system 17 in this embodiment, senses the intensity of light emitted from the illumination system 13 throughout the patient's cardiac cycle as the light is transmitted, scattered (e.g., forward-scattered or back-scattered), and/or reflected through the subcutaneous tissue and pulsating artery 2, as well as other structures between the sensor and the light source. The sensor may preferably be a silicon detector, similar to the detector in a pulse oximeter probe. Alternatively, any other suitable detector that will detect energy from the energy delivery system may be satisfactory to practice particular embodiments of the invention.

In various embodiments, the ultrasound imaging system 15 provides the device with accurate imaging of the artery throughout the cardiac cycle, but especially in both systole and diastole in the case of an artery, or during vessel distention and collapse in the case of a vein, which are the timepoints of maximum and minimum vessel diameter respectively. The ultrasound transducers (which may, for example, be high-frequency ultrasound transducers having a frequency of, for example, 8 MHz or higher) are preferably adapted to provide an accurate resolution of the cross-section of the vessel, which is useful in accurately calculating the volume change of the vessel between systole and diastole, and/or during vessel distention and collapse. This information may be useful calculating hemoglobin concentration, or the concentration of any other selective energy absorber. The ultrasound imaging system 15 may, for example, yield data as two-dimensional (otherwise called B-mode ultrasound) or the ultrasound imaging system 15 may be a three-dimensional ultrasound imaging system. Additionally, a three-dimensional ultrasound imaging system that measures motion is called four-dimensional ultrasound and may be used with particular embodiments of the present invention in place of the above noted two-dimensional ultrasound imaging system or three-dimensional ultrasound imaging system. Any other suitable ultrasound imaging system may also be used in particular embodiments of the invention.

In particular embodiments, data from the ultrasound imaging system 15 may be transferred to an image analysis and edge detection system 19. In various embodiments, this system 19 contains software known to those skilled in the art for dynamically measuring the long- and short-axis cross-sections of the insonated vessels in both systole and diastole, or during vessel distention and collapse. This measurement leads to a calculation of the volume changes experienced by the blood within the insonated vessels during the vessel distension-collapse cycle.

In various embodiments, the overall system may further include a data analysis system 21 that, in various embodiments, is a computer system that is adapted to receive input from both the energy (photometric) sensor system 17 and the image analysis and edge detection system 19. The data analysis system 21 then takes this data and calculates an absorber (e.g., total hemoglobin) concentration by calculating a ratio of: (1) the measured mass change (from the photometric sensor system 17) for a vessel distention and collapse cycle; and (2) the vessel volume change (from the image analysis and edge detection system 19) from the same cycle. An appropriate nomogram is then used to accurately predict and report the calculated absorber concentration value (e.g., the blood total hemoglobin concentration).

The calculated result (e.g., total hemoglobin concentration) is then sent to the output system 23, for either display by the display system 25 and/or the result is stored in data storage 27 for future reference. In various embodiments, the data storage 27 system also has connectivity to other medical devices with common connectors including USB, RS232, and/or infrared interfaces.

FIG. 2, which is a schematic side view of one embodiment of the present invention, shows a cross-section of this embodiment of the invention in conjunction with a longitudinal cross-section of a patient's forearm 41, including a longitudinal cross-section of the radial artery 2. The device 29 is attached to the forearm 41 and ultrasound gel 11 is applied between the ultrasound transducer 6 and the skin 1. Any suitable ultrasound-compatible coupling compound or interface may be used in place of or in conjunction with ultrasound gel 11.

In particular embodiments, light 8 from the light source 4 is emitted throughout several cardiac cycles of systole and diastole, while the light 8 is aimed toward the radial artery 2 as shown in FIG. 2. The light is scattered and absorbed in the tissues, including the subcutaneous tissue 3, but some of the light rays 9 proceed as drawn, reflecting from the tissues, and excite the sensor 5. Simultaneously with the photometric measurements as described above, the ultrasound imaging system 15 is imaging the artery 2 with the high frequency ultrasound transducer 6 during the cardiac cycle including both systole and diastole.

In FIG. 2, the light source 4 and the sensor 5 are on opposite sides of the ultrasound transducer 6 such that the artery imaged, and the cross-sectional measurements made by ultrasound, represent a close approximation of the change in mass of the hemoglobin species. In various embodiments, the photometric and ultrasound systems are incorporated into the same device for ease of use as well as cost savings. However, in other embodiments, the photometric and ultrasound systems may be physically separate from each other. These data are then sent via the ultrasound cord 39 to the image analysis and edge detection system 19 (see FIG. 1) for cross-sectional area determination of the artery 2 during systole and diastole.

FIG. 3 is an illustrative top view of FIG. 2. The device 29 is placed along the course of the radial artery 2, in conjunction with the patient's forearm 41, with the patient's hand 7 positioned as shown. Illustrated in FIG. 3 is an ultrasound cord 39, which is included in various embodiments of the invention. This ultrasound cord 39 sends information to the image analysis and edge detection system 19. In various embodiments, the sensor cord 8 is the conduit for communication between both the sensor 5 and the light source 4, and the data analysis system 21, which, in various embodiments, also serves to drive the device's illumination system 13 and to analyze data from the photometric sensor system 17 (see FIG. 1).

FIG. 3 also reveals that, in this embodiment, the shown device placed against the patient is a small unit, making it convenient for the healthcare provider. It should be understood that the ultrasound cord 39 and sensor cord 8 may, in particular embodiments, be replaced with a wireless data transmission system or any other suitable data transmission system.

FIGS. 4A and 4B show an axial cross-section of a portion of the patient's forearm 41. In FIG. 4A, the radial artery 2 is shown in diastole, when the vessel's cross-section is at its smallest diameter. The ultrasound transducer 6 is illustrated against the patient's skin 1, with ultrasound gel 11 between the transducer 6 and skin 1 to make a good contact surface for transmitting the ultrasound image to the ultrasound transducer 6. FIG. 4b shows the artery 2 during systole, when the artery's cross-section is at its maximum diameter. Again, the skin 1, gel 11 and ultrasound probe 6 are illustrated. In this embodiment, the ultrasound imaging system 15 forms an image during the cardiac cycle and allows accurate measurement of the cross-sectional area difference of the artery between systole and diastole.

FIG. 5 shows a typical tracing of the light sensor output when the light source and sensor from a standard pulse oximetry probe is placed over the patient's radial artery. The tracing shows a series of peaks 49 and troughs 33. The displayed peaks at 49 correspond to systole and the troughs at 33 to diastole. The period between peak 49 to consecutive peak 49 is one cardiac cycle. The peak 49 occurs approximately at the same time-period as the maximum diameter of the radial artery 2 as shown in the right panel of FIG. 4.

FIG. 6 is a sample graph of Δmass/Δvolume vs. hemoglobin concentration values as may be derived from particular embodiments of the present invention. By sampling a series of patients with the device at a number of different blood hemoglobin species concentrations, the nomogram which displays the species Δmass:Δvolume vs. the laboratory-measured blood hemoglobin species value is derived. In particular embodiments, once this graph is created for the device, the concentration of any unknown blood hemoglobin species can be measured by using the device to measure the change in species mass during a cardiac cycle, dividing that value by the change in volume and, using the previously derived nomogram, the unknown hemoglobin species concentration can be calculated.

FIG. 7 illustrates how, in one embodiment of the invention, pressure directly over a patient's artery causes the arterial pulsation to be enhanced. The device can provide a pressure of, for example, 10 grams to 2 kilograms adjacent an artery by either its own weight or by pressure from another mechanism. (FIG. 8 illustrates two pressure transducers 45 that are used to measure the pressure over the site of measurement.) Again, regarding FIG. 7, the change from systole to diastole is often more accentuated, increasing the change in plethysmogram amplitude and arterial pulsation during the cardiac cycle and making the measurement more robust. Furthermore, the light signal change is larger with this direct pressure over the artery. FIG. 7a shows the artery 2 prior to pressure 35 above the artery 2 by the ultrasound transducer 6, with gel 11 shown between the transducer 6 and the skin 1 of the forearm 41. FIG. 7B shows the increase in cross-section of the radial artery 2 at the same point in the cardiac cycle as FIG. 7A with an increase in pressure from the transducer 6 against the skin 1. Accordingly, in various embodiments, compression augments pulsatility by compressing the artery (up to the mean arterial pressure) to a smaller diastolic cross-sectional area (volume) which causes an increased compliance as the vessel is "unloaded" and then expands with pulsation to a much greater diameter—when compared to baseline diameter.

FIG. 8, which shows a device according to an alternative embodiment of the invention, is shown with two pressure transducers 45 incorporated into the device to monitor the pressure upon the artery 2 against the skin 1. Particular embodiments of the invention may use any number of pressure transducers 45 to practice various embodiments of this invention. This may be advantageous because it may help to assure that proper contact (not too little and not too much contact) of the ultrasound machine with the skin has been achieved. Furthermore, a pressure transducer as described above can be utilized to define the optimal pressure to accentuate the pulsation of the artery 2 with direct pressure from the device. A feedback loop may be incorporated into particular embodiments of the invention to maximize the accentuation in change of the artery 2 diameter between systole and diastole with pressure. In particular embodiments, the information from the pressure transducer(s) 45 is relayed via the sensor cord 8 to the data analysis system 21, which also serves to drive and control the pressure transducer 45. A plurality of pressure sensors may be employed to assure that pressure is uniformly applied by the device on the patient's skin. Pressure sensors that are embedded into the device (e.g., adjacent the ultrasound transducer) may also be used to measure intravascular pressure from the same device.

A self-testing function may be included in particular embodiments of the invention that tests the quality of image. If the quality of the image is not meeting preset specifications, then an error message is given. (In some cases, the quality of the image may possibly be affected by placement of the device on the skin or the ultrasound gel 11—or other ultrasound coupling interface—drying during the course of measurements.) In addition, any ultrasound coupling material may be used in various embodiments of the invention in place of the ultrasound gel 11 or in conjunction with the ultrasound gel 11.

FIGS. 9A and 9B are illustrations of the measurement utilizing a DC component to make a blood hemoglobin species measurement. It should be understood that the light source 4 and sensor 5 components of the device 29 are present in this embodiment, but not shown in FIG. 9, for purposes of simplicity. The ultrasound transducer 6 is shown exerting only contact pressure on the skin superficial to the vascular structures (artery 2 and veins 47). Although the radial artery 2 is a consistent structure in most patients, the veins 47 are more variable, sometimes occurring as two or four structures (or any number of veins) on either side of the radial artery 2 as shown in FIG. 9A. In FIG. 9B, pressure is exerted on the skin above the artery 2 and the veins 47. (As a result, the veins are collapsed as shown in FIG. 9B.) This pressure is measured by the pressure transducer 45. The pressure required to compress the veins is generally less than 40 mm Hg but will vary between individuals with differences in the depth of the veins, venous pressure and tissue compliance. The volume of blood contained in the veins can exceed the volume of blood in the artery by 100 percent or more. The technique of measuring the intravascular volume we describe can, in particular embodiments, advantageously exploit this relationship.

The signal produced by passing light through a complex living tissue is typically comprised of two major components. There is a small alternating current (AC) and very large direct current (DC) signal. The AC signal varies with time as absorber volume or concentration changes and represents a smaller portion than the DC portion of the entire signal. The source of this variation is from blood and its energy absorbers entering and then departing the light path with each pulse—also termed the "pulse-added" volume. The DC component does not substantially vary with time. As well described in the literature, it results from light absorption by time-invariant tissues which include muscle, tendon, skin, fat, venous blood, and arterial blood that remains in the artery during diastole.

The DC component is, in various embodiments, used only for signal normalization when multiple light sources are used, but is otherwise relatively invariant over time. However, if tissues are compressed to eliminate venous (and some arterial) blood, a large DC signal change will often be observed. If the compression maneuver brings the photo emitter-detector pair closer to one another, in various embodiments, corrections for that light intensity increase are made. But, in particular embodiments, if the emitter-detector pair remain fixed in separation, as is described in one advantageous orientation (see FIGS. 2, 3, 8, and 10), the DC signal change observed will be predominantly from the blood eliminated from the veins (and artery). This light intensity signal change represents the mass of absorber change while the vessel's altered dimensions provide the volume change. These large signals can be used advantageously to improve absorber mass measurement accuracy and to quantify absorbers that produce a weaker signal. Furthermore, the DC signal offers a chance to view the venous side of a tissue bed and will create an opportunity to measure tissue oxygen extraction, which is a measure of stress and can be a valuable management tool in the critically ill patient.

FIG. 10 is another embodiment of the device. In this embodiment, a plurality of ultrasound transducers is used to enhance the image quality. Shown is a short axis cross-sectional measurement of the artery made together with a long axis cross-sectional measurement. Referring to FIG. 10, a first set of ultrasound crystals 49 are oriented to image the longitudinal aspect of the radial artery 2, while a second set of ultrasound crystals 51 are oriented to image the cross-section of the radial artery 2. One advantage of this embodiment is that there is more accurate three dimensional imaging of the artery obtained, since with both longitudinal cross-sectional and axial cross-section are directly measured by ultrasound, a very accurate volume measurement can be made. In addition, less accuracy in placing the device over the artery may be required. Other combinations of transducers in orientation, frequency, or power may be used to optimize tissue characterizations. Tissue includes any aggregate of similar cells and cell products forming a definite kind of structural material with a specific function and includes blood. Transducers added with lower frequency may, in various embodiments, allow imaging of deeper structures. Orientation of the transducer may advantageously add measures of intravascular flow, pressure, and peripheral vascular resistance. These parameters may be of significant value in guiding clinical care.

Another alternative embodiment of the invention utilizes three-dimensional ultrasound for the measurement of the volume measurement. Three-dimensional ultrasound imaging works by acquiring two-dimensional data in a series of individual scans (commonly called B-scans) of a volume of tissue. Forming the three-dimensional images may, in certain embodiments, require location of each individual two-dimensional image using known acquisition geometries.

Additional Information on Structure and Use of Various Embodiments

Various embodiments of devices for measuring the concentration of energy absorbers (e.g., hemoglobin) in blood may be configured somewhat differently than the examples discussed above. It is noted that the energy absorber measurement device shown in FIG. 3 depicts the device as being configured so that, when the device is in proper use (e.g., when the device is being used to measure the concentration of energy absorbers in a particular structure such as a vascular structure), the sensor 5 (e.g., photodetector) and the light source 4 are positioned in a common plane with: (1) each other; and (2) a central axis of the structure (e.g., radial artery 2) being imaged by the device's ultrasound transducer 6. In such embodiments, a line that extends between the sensor 5 and the light source 4 may be at least substantially parallel to the central axis of the structure being imaged (e.g., the radial artery 2). In various examples of such embodiments, the device is configured: (1) so that when the device is in proper use, at least some of the light produced by the light source 4 passes through a portion of the structure (e.g., radial artery 2) being imaged; and (2) so that, in doing so, the light moves at least substantially parallel (e.g., parallel) to the direction of blood flow through the artery 2.

However, in alternative embodiments, the device may be configured so that, when the device is in proper use, the sensor 5 (e.g., photodetector) and the light source 4 are not positioned in a common plane with: (1) each other; and (2) a central axis of the structure (e.g., radial artery 2) being imaged by the device's ultrasound transducer 6. In such embodiments, a line that extends between the sensor 5 and the light source 4 may be at least substantially perpendicular to the central axis of the structure (e.g., radial artery 2) being imaged by the device's ultrasound transducer 6. In various examples of such embodiments, the device is configured: (1) so that when the device is in proper use, at least some of the light produced by the light source 4 passes through a portion of the radial artery 2 being imaged; and (2) so that, in doing so, the light moves at least substantially perpendicular (e.g., perpendicular) to the direction of blood flow through the artery 2.

In light of the above, it should be understood that in particular embodiments, the light source/sensor assembly may either be: (1) at least substantially in-line with (e.g., in-line with) the structure (e.g., radial artery 2) being imaged by the ultrasound transducer 6; or (2) positioned so that the light source 4 and sensor 5 "straddle" the portion of the structure being imaged by the device.

Furthermore, in the embodiment shown in FIG. 3, the light source/sensor assembly is positioned directly over the portion of the structure (e.g., radial artery 2) that is being imaged by the ultrasound transducer 6. In alternative embodiments, the light source/sensor assembly may be positioned so that this assembly is offset from the structure being imaged on either side of the structure.

In various embodiments of the invention, such as the embodiment shown in FIG. 3, the light source 4 and sensor 5 are maintained a fixed distance apart by the physical structure of the energy absorber measurement device. However, in alternative embodiments, the device may be adapted to allow the user to selectively reposition the light source 4 and/or the sensor 5 in relation to other components of the device. This may allow a user to selectively change the distance between the light source 4 and the sensor 5. This feature may make it easier to optimize the performance of the device by adjusting the path of the light produced by the light source 4 to account for the depth of the structure (e.g., artery) being imaged. In a particular embodiment of the invention, the light source 4 and sensor 5 (e.g., photo detector) are separated by a distance that is equal to two times the depth (or typical depth) of a structure (e.g., artery) that is to be imaged by the device's ultrasound transducer.

In various embodiments of the invention, such as the embodiment shown in FIG. 3, the light source 4 and the sensor 5 are shown on opposite sides of the ultrasound transducer 6. However, in particular embodiments of the invention, the light source 4 and the sensor 5 are both disposed adjacent the same side of the ultrasound transducer 6.

It is noted that the sensor 5 (e.g., photodetector) of various embodiments (such as the embodiment of FIG. 3) is shown positioned distal to the device's light source 4. However, in other embodiments, the sensor 5 may be positioned proximal to the light source 4.

As noted above, different configurations of ultrasound transducers may be used in any of the embodiments described herein. For example, the ultrasound transducer may be configured to produce: (1) a longitudinal cross-sectional image of the structure (e.g., radial artery) being imaged; (2) an axial cross-sectional image of the structure (e.g., radial artery) being imaged; (3) both a longitudinal and an axial cross-sectional image of the structure being imaged; or (4) any other suitable image of the structure being imaged.

CONCLUSION

Many modifications and other embodiments of the inventions set forth herein will come to mind to one skilled in the art to which these inventions pertain having the benefit of the teachings presented in the foregoing descriptions and the associated drawings. For example, while at least some of the above-described devices are adapted to be used manually by a user (e.g., the pressure provided by the device on the structure being imaged is generated manually by the user), other embodiments of the device may be adapted to provide one or more aspects of the device's functionality in an automated manner.

As another example, while various embodiments described above discuss using ultrasound devices for imaging purposes, the device may use (e.g., comprise) imaging devices other than ultrasound transducers. For example, devices and methods according to various embodiments of the invention may use (e.g., comprise) an MRI device or any other suitable imaging device in implementing the methods described above.

Similarly, although various embodiments above discuss using a pulse oximeter as the device's photometric device, any other suitable photometric device (or other suitable device) may be used in other embodiments of the invention.

Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method for use in determining a tissue energy absorber concentration in an individual's blood, said method comprising:
    (a) using a photometric device to measure a change in mass of said tissue energy absorber within a particular volume of said individual's blood between a first point in time and a second point in time, said particular volume of blood being blood within at least a first particular portion of at least one vascular structure, said vascular structure comprising at least one of said individual's vessels;
    (b) using an ultrasound imaging device to measure a change in interior volume, between about said first point in time and about said second point in time, of a second particular portion of said at least one vascular structure, wherein the ultrasound imaging device measures a volume of the second particular portion of the at least one vascular structure by measuring a long-axis cross-sectional area and a short-axis cross-sectional area of the second particular portion of the at least one vascular structure, said second particular portion at least generally corresponding to said first particular portion; and
    (c) using said measured change in said mass of said tissue energy absorber, and said measured change in interior volume to determine at least an approximate blood total concentration of said tissue energy absorber within said individual's blood.

2. The method of claim 1 wherein said Step (b) comprises using said ultrasound imaging device to measure said change in interior volume between said first point in time and said second point in time.

3. The method of claim 1 wherein said first particular portion and said second particular portion each comprising substantially the same portion of said at least one vascular structure.

4. The method of claim 1 wherein said first particular portion comprises said second particular portion.

5. The method of claim 1 wherein said second particular portion comprises said first particular portion.

6. The method of claim 1 wherein said step of using said ultrasound imaging device to measure said change in interior volume comprises:
    using said cross-sectional area to make a determination of said change in interior volume.

7. The method of claim 1 wherein:
    said photometric device comprises a light source and a light sensor; and
    said step of using a photometric device to measure a change in mass of said tissue energy absorber comprises:
        positioning a light source adjacent a particular side of an extremity of said individual;
        positioning a light sensor adjacent said particular side of said extremity; and
        while said light source and light sensor are each positioned adjacent said particular side of said extremity, using said light source and said light sensor to measure said change in mass of said tissue energy absorber.

8. The method of claim 1 wherein said ultrasound imaging device is configured for ultrasound imaging at least about 8 MHZ.

9. The method of claim 1 wherein:
    said at least one vascular structure comprises an artery;
    said artery is in a substantially systolic orientation at said first point in time;
    said artery is in a substantially diastolic orientation at said second point in time; and
    said step of using said ultrasound imaging device to measure said change in interior volume comprises:
        using said ultrasound imaging device to measure a first cross-sectional area of said artery at said first point in time;
        using said ultrasound imaging device to measure a second cross-sectional area of said artery at said second point in time; and
        using said first and second cross-sectional area to make a determination of said change in interior volume.

10. The method of claim 1 wherein:
    said photometric device comprises a light source and a light sensor; and
    said light source and said light sensor are substantially in the same plane as said ultrasound device during the execution of Steps (A) and (B).

11. The method of claim 1 wherein a light measurement for making the mass change measurement is made through the same tissue bed as the ultrasound measurement of said change interior volume.

12. The method of claim 1 wherein the energy absorber is oxyhemoglobin and deoxyhemoglobin together, or functional total hemoglobin.

13. The method of claim 1 wherein the energy absorber is oxyhemoglobin.

14. The method of claim 1 wherein the energy absorber is deoxyhemoglobin.

15. The method of claim 1 wherein the energy absorber is fetal hemoglobin.

16. The method of claim 1 wherein the energy absorber is methemoglobin.

17. The method of claim 1 wherein the energy absorber is carboxyhemoglobin.

18. The method of claim 1 wherein the energy absorber is bilirubin.

19. The method of claim 1 wherein:
said vascular structure is an artery of said individual; and
said method further comprises executing pressure directly over said artery while executing said Steps A and B to cause the artery to unload and form an augmentation of a pulsation of said artery during execution of Steps A and B.

20. The method of claim 19 wherein said pressure causes an augmentation of a pulsation in a diastolic cross-section of said artery during the execution of Steps A and B.

21. The method of claim 19 wherein said pressure causes an increase in a change of a cross-section of said artery from diastole to systole during the execution of Steps A and B.

22. A method of determining tissue energy absorber concentration in an individual, said method comprising:
(a) at a first point in time, using a photometric device to measure a first mass of said tissue energy absorber within a first particular volume of said individual's blood, said first particular volume of blood being blood within at least a first particular portion of at least one vascular structure at said first point in time, said vascular structure comprising at least one of said individual's vessels;
(b) at about said first point in time, using an ultrasound imaging device to measure a first interior volume of a second particular portion of said at least one vascular structure, wherein the ultrasound imaging device measures a volume of the second particular portion of the at least one vascular structure by measuring a long-axis cross-sectional area and a short-axis cross-sectional area of the second particular portion of the at least one vascular structure, said second particular portion at least generally corresponding to said first particular portion;
(c) at a second point in time, using said photometric device to measure a second mass of said tissue energy absorber within a second particular volume of said individual's blood, said second particular volume of blood being blood within said at least a first particular portion of said at least one vascular structure at said second point in time;
(d) at about said second point in time, using said ultrasound imaging device to measure a second interior volume of said second particular portion of said at least one vascular structure;
(e) using said first and second mass measurements to determine a change in mass of said tissue energy absorber;
(f) using said first and second interior volume measurements to determine a change in interior volume; and
(g) using said change in mass of said tissue energy absorber and said change in interior volume to determine at least an approximate blood total concentration of said tissue energy absorber within said individual's blood.

23. The method of claim 22, wherein said method further comprises, during said steps (c) and (d), exerting a particular external pressure on said first and second particular portions of said at least one vascular structure, said particular pressure being greater than any external pressure that is exerted on said first and second particular portions of said at least one vascular structure during said steps (a) and (b).

24. The method of claim 23, wherein, during each of steps (b) and (d), a cross-sectional area of a blood vessel measured by said ultrasound imaging device is used to make a determination of a volume of said second particular portion of said at least one vascular structure.

25. The method of claim 22, wherein said step (e) comprises using DC components of signals associated with said first and second mass measurements to determine said change in mass of said tissue energy absorber.

26. The method of claim 22, wherein said steps (b) and (d) comprise:
using said cross-sectional area to make a determination of an interior volume of said second particular portion of said at least one vascular structure.

27. The method of claim 22 wherein:
said photometric device comprises a light source and a light sensor; and
said steps (a) and (c) each comprise:
positioning said light source adjacent a particular side of an extremity of said individual;
positioning said light sensor adjacent said particular side of said extremity; and
while said light source and light sensor are each positioned adjacent said particular side of said extremity, using said light source and said light sensor to measure a mass of said tissue energy absorber within said first particular portion of said at least one vascular structure.

28. The method of claim 22 wherein said ultrasound imaging device is at least an 8 MHz ultrasound imaging device.

29. The method of claim 22 wherein the energy absorber is oxyhemoglobin and deoxyhemoglobin together, or functional total hemoglobin.

30. The method of claim 22 wherein the energy absorber is oxyhemoglobin.

31. The method of claim 22 wherein the energy absorber is deoxyhemoglobin.

32. The method of claim 22 wherein the energy absorber is fetal hemoglobin.

33. The method of claim 22 wherein the energy absorber is methemoglobin.

34. The method of claim 22 wherein the energy absorber is carboxyhemoglobin.

35. The method of claim 22 wherein the energy absorber is bilirubin.

* * * * *